United States Patent
Elenbaas et al.

(10) Patent No.: US 10,055,838 B2
(45) Date of Patent: Aug. 21, 2018

(54) REGISTRATION OF MEDICAL IMAGES

(71) Applicant: KONINKLIJKE PHILIPS N.V., Eindhoven (NL)

(72) Inventors: Thijs Elenbaas, Nijmegen (NL); Markus Johannes Harmen Den Hartog, Eindhoven (NL); Martijn Van Geloof, Boxtel (NL); Robin Pieter De Paus, Breda (NL)

(73) Assignee: Koninklijke Philips N.V., Eindhoven (NL)

( * ) Notice: Subject to any disclaimer, the term of this patent is extended or adjusted under 35 U.S.C. 154(b) by 144 days.

(21) Appl. No.: 15/031,282

(22) PCT Filed: Nov. 7, 2014

(86) PCT No.: PCT/EP2014/074067
§ 371 (c)(1),
(2) Date: Apr. 22, 2016

(87) PCT Pub. No.: WO2015/071191
PCT Pub. Date: May 21, 2015

(65) Prior Publication Data
US 2016/0275684 A1 Sep. 22, 2016

(30) Foreign Application Priority Data
Nov. 14, 2013 (EP) .................................... 13192904

(51) Int. Cl.
*G06T 7/00* (2017.01)
*A61B 6/00* (2006.01)
(Continued)

(52) U.S. Cl.
CPC .......... *G06T 7/0012* (2013.01); *A61B 6/5247* (2013.01); *G06T 7/33* (2017.01);
(Continued)

(58) Field of Classification Search
CPC ......... A61B 6/4441; A61B 6/504; A61B 6/02; A61B 6/485; A61B 6/5247;
(Continued)

(56) References Cited

U.S. PATENT DOCUMENTS 6,340,994 B1 * 1/2002 Margulis .................. G09G 3/20
348/625
7,453,456 B2 * 11/2008 Petrov ...................... G06K 9/20
345/419
(Continued)

OTHER PUBLICATIONS

Markelj et al., 2010, "A review of 3D/2D registration methods for image-guided intervention". (pp. 642-661).*
(Continued)

*Primary Examiner* — Manav Seth

(57) ABSTRACT

A method for registration of medical images comprises: receiving a 2D X-ray image (20) acquired with a medical 2D imaging device (14) under a first view direction; filtering the 2D X-ray image (20), such that high frequency components of the 2D X-ray image are emphasized with respect to low frequency components of the 2D X-ray image; receiving a 3D image (16) acquired with a medical 3D imaging device (12); generating a 2D projection image (26) from the 3D image, wherein the 2D projection image is generated with a second view direction; overlaying the filtered 2D X-ray image and the 2D projection image; providing functionality for changing the second view direction, such that the 2D projection image is registered with the filtered 2D X-ray image.

14 Claims, 2 Drawing Sheets

(51) Int. Cl.
    *G06T 11/00*    (2006.01)
    *G06T 7/33*    (2017.01)
(52) U.S. Cl.
    CPC ........ *G06T 11/008* (2013.01); *G06K 2209/40* (2013.01); *G06T 2200/04* (2013.01); *G06T 2207/10072* (2013.01); *G06T 2207/10081* (2013.01); *G06T 2207/10088* (2013.01); *G06T 2207/10124* (2013.01)
(58) Field of Classification Search
    CPC . A61B 2090/367; A61B 6/032; A61B 6/5205; G06K 2209/40; G06T 11/008; G06T 2211/404; G06T 2207/10081; G06T 15/00; G06T 2207/20182; G06T 2207/20216; G06T 7/0028; G06T 7/33; G06T 7/0012; G06T 2200/04; G06T 2207/10072; G06T 2207/10088; G06T 2207/10124
    See application file for complete search history.

(56) References Cited

U.S. PATENT DOCUMENTS

| | | | | |
|---|---|---|---|---|
| 8,654,119 | B2* | 2/2014 | Mistretta | A61B 6/02 345/419 |
| 8,830,234 | B2* | 9/2014 | Mistretta | A61B 6/02 345/419 |
| 2005/0271302 | A1 | 12/2005 | Khamene et al. | |
| 2010/0061611 | A1* | 3/2010 | Xu | G06T 19/00 382/131 |
| 2010/0201786 | A1* | 8/2010 | Schaefer | G06T 7/30 348/47 |
| 2010/0296623 | A1* | 11/2010 | Mielekamp | A61B 6/032 378/4 |
| 2011/0313285 | A1 | 12/2011 | Fallavollita et al. | |
| 2012/0022366 | A1 | 1/2012 | Pfister | |

OTHER PUBLICATIONS

Markelj P. et al., "A review of 3D/2D registration methods for image-guided interventions", Medical Image Analysis, Oxford University Press, vol. 16, No. 3, 2012, pp. 642-661.

Joskowicz, L. et al., "Computer integrated revision total hip replacement surgery: preliminary report".

Dalvi, R., "Novel approaches for multi-modal imaging and fusion in orthopaedic research for analysis of bone and joint anatomy and motion", Thesis—The University of British Columbia—Vancouver, 2009.

Wu, J. et al., "Assessing the intrinsic precision of 3D/3D rigid image registration results for patient setup in the absence of a ground truth", Med. Phys. Jun. 2010: 37(6): 2501-2508.

Taylor, R.H., et al., "Computer-integrated revision total hip replacement surgery: concept and preliminary results", Medical Image Analysis (1999), vol. 3, No. 3, pp. 301-319.

* cited by examiner

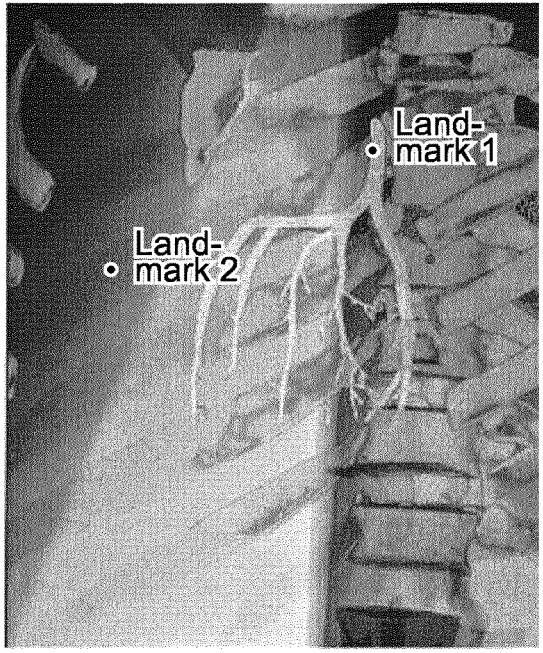
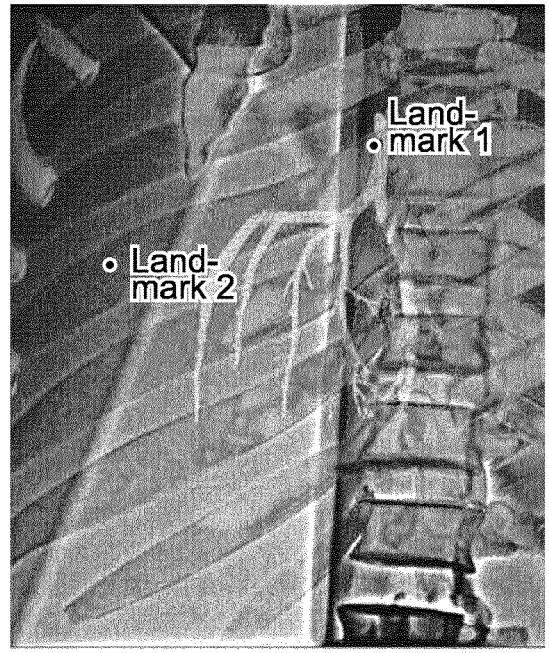
Fig. 3A                    Fig. 3B
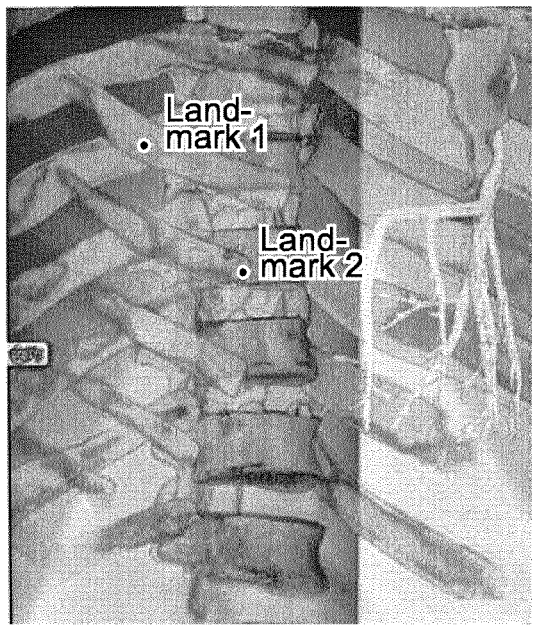
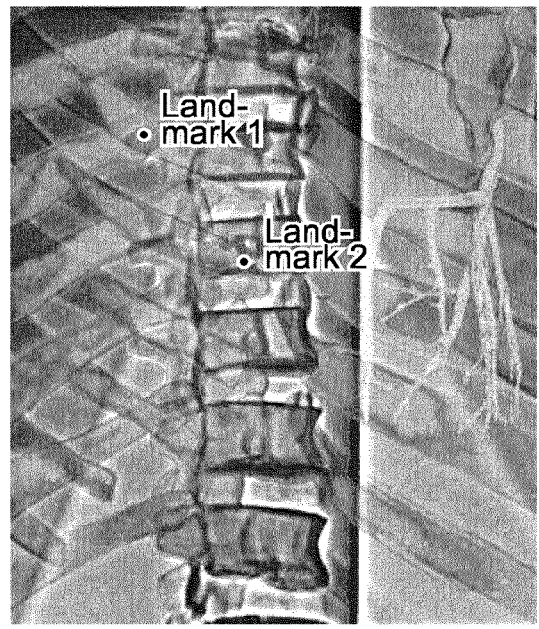
Fig. 4A                    Fig. 4B

REGISTRATION OF MEDICAL IMAGES

CROSS-REFERENCE TO PRIOR APPLICATIONS

This application is the U.S. National Phase application under 35 U.S.C. § 371 of International Application No. PCT/EP2014/074067, filed on Nov. 7, 2014, which claims the benefit of European Patent Application No. 13192904.4, filed on Nov. 14, 2013. These applications are hereby incorporated by reference herein.

FIELD OF THE INVENTION

The invention relates to a method, a computer program, a computer-readable medium and a device for registration medical images.

BACKGROUND OF THE INVENTION

During a procedure that uses multiple imaging modalities, for example CT and live X-ray, a physician may need to register the modalities. For example, when using an interventional X-ray device, in particular a C-arm device, the physician may move the C-arm to a certain angulation that gives him a clear view on landmarks in a body of a patient that can be used for registration, for example the pelvic bone. He will then acquire an exposure run or a single shot image. Next, the physician may move the C-arm to a different angulation that may be sufficiently different (e.g. more than 45 degrees difference) and shoot another exposure or single shot.

Both X-ray runs may be shown in different viewports on a display device, where they are blended or overlaid with projection images of the CT volume (3D) image. The physician may move the CT image in both views such that it optimally overlaps the live X-ray images. The visual markers that the physician uses to determine optimal overlap are usually bony landmarks, such as the pelvis, spine or thorax. While the pelvic bones are relatively easy to distinguish in an X-ray image, the spine and thorax may be more difficult, especially with obese patients or low-dose X-ray protocols.

SUMMARY OF THE INVENTION

Low contrast features in X-ray images, such as the edges of spinal discs or the outlines of thoracic bones, may be difficult to distinguish even for trained physicians, especially when these ridges are (nearly) perfectly aligned with outlines in a projection image of a 3D image.

There may be a need for a registration method, which helps an operator to register 2D X-ray images with each other.

Such a need may be met by the subject-matter of the independent claims. Further embodiments of the invention are evident from the dependent claims and the following description.

An aspect of the invention relates to a method for registration of (in particular medical) images.

According to an embodiment of the invention, the method comprises the steps of: receiving a 2D (two-dimensional) image acquired with a medical 2D imaging device under a first view direction; filtering the 2D image, such that high frequency components of the 2D image are emphasized with respect to low frequency components of the 2D image; receiving a 3D (three-dimensional) image acquired with a medical 3D imaging device; generating a 2D projection image from the 3D image, wherein the 2D projection image is generated with a second view direction; overlaying the filtered 2D image and the 2D projection image; and providing functionality for changing the second view direction, such that the 2D projection image is registered with the filtered 2D image.

During a registration procedure, in which a 2D image such as an X-ray image is aligned/registered with a 3D image (or the 2D projection thereof), the X-ray image is filtered in a way that bony landmarks in the X-ray image may be boosted such that these landmarks become more visible in the blended/overlaid image. This may serve to better visualize to an operator, if the overlap is optimal, thereby helping the operator to obtain an optimal registration. In particular, by boosting specific higher frequency components of the image while suppressing lower frequency components, the contrast of bony outlines may be improved to such an extent that they become discernible even when overlaid by a 3D volume image that may be so similar and well registered, that all relevant (bony) edges in 2D projection image and 3D image fully overlap.

Further aspects of the invention relate to a computer program, which, when being executed by a processor, is adapted for performing the steps of the method as described in the above and in the following, and a computer-readable medium, on which such a computer program is stored. A computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g. the Internet, which allows downloading a program code.

A further aspect of the invention relates to an image processing device adapted for performing the steps of the method as described above and in the following. For example, the controller of an X-ray device may be also the image processing device or the image processing device may be a separate workstation. In the controller or the workstation, corresponding software may be running.

It has to be understood that features of the image processing device as described in the above and in the following may be features of the method, computer program and the computer-readable medium as described in the above and in the following as well as vice versa.

These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

FIGS. 3A and 4A show overlay images.

FIGS. 3B and 4B show overlay images generated with a method for registration of medical images according to an embodiment of the invention.

The reference symbols used in the drawings, and their meanings, are listed in summary form in the list of reference signs. In principle, identical parts are provided with the same reference symbols in the figures.

DETAILED DESCRIPTION OF EMBODIMENTS

Figure 1:
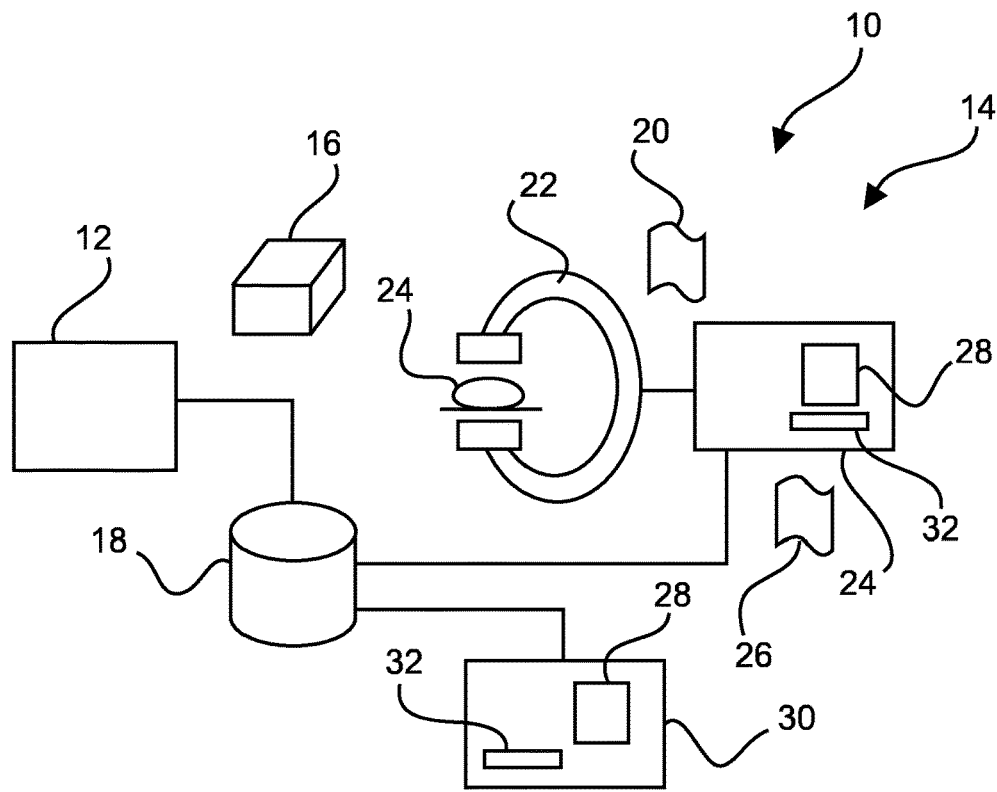
FIG. 1 schematically shows a system with image processing devices according to an embodiment of the invention.

FIG. 1 schematically shows a system 10 comprising a 3D imaging device 12, and a 2D imaging device 14.

The 3D imaging device 10 may be a CT (computer tomography) or MRT (magnet resonance tomography) device and/or may be located remote from the 2D imaging device 12. For example, both devices may be situated in different rooms of a clinic or at different doctor's offices.

The 3D imaging devices is adapted for generating 3D images 16. A 3D image 16 may comprise voxels, each voxel comprising at least one intensity value associated to three coordinates. The 3D image data 16 may be acquired at a different time as the 2D imaging device 12 is used and/or may be stored in database 18.

The 2D imaging device 14 may be an X-ray device for acquiring 2D images 20, for example a C-arm device with a C-arm 22 that may be moved around a patient 24 for taking X-ray images 20 of the patient 24 from different directions. A 2D image 20 may comprise pixels, each pixel comprising at least one intensity value associated with two coordinates.

The 2D imaging device 14 has a controller 24 that may control the C-arm and/or may generate the 2D images 20. The controller 24 is additionally adapted for receiving the 3D image 16, for example from the database 18.

The controller 24 is adapted for generating 2D projection images 26 from the 3D image 16 and/or for displaying the 2D projection images 26 and the 2D images 20 on a display device 28.

The 3D image 16 and the 2D images 20 are acquired from the same object of interest/part of the patient 24 and the controller 24 provides functionality for overlaying a 2D image acquired with the 2D imaging device 14 with a 2D projection image 26 that both have the same viewing direction.

It has to be understood that the functionality of the controller 24 with respect to image processing may also be performed by a workstation 30 (eventually remote from the device 12 and 14) that may receive both the 3D image 16 and the 2D images(s) 20. Both the controller 24 and the workstation may be seen as image processing devices 24, 30. For example, also the 2D images 20 may be stored in the database 18 by the controller 24 and fetched afterwards by the workstation 30. Also the workstation 30 may have a display device 28 or may be interconnected with a display device 28 for displaying the 2D images 20, 26.

Furthermore, both the controller 24 and the workstation 30 may provide functionality for moving, scaling and/or rotating the 2D projection image 26 and the 2D image 20 with respect to each other such that the two images 26, 20 may be aligned and/or registered with respect to each other.

In particular, the controller 24 and the workstation may comprise an input device 32, with which an operator can select a specific viewport on the 3D image. In such a way, the operator may translate, rotate and/or scale the 3D image with respect to the 2D X-ray image.

Figure 2:
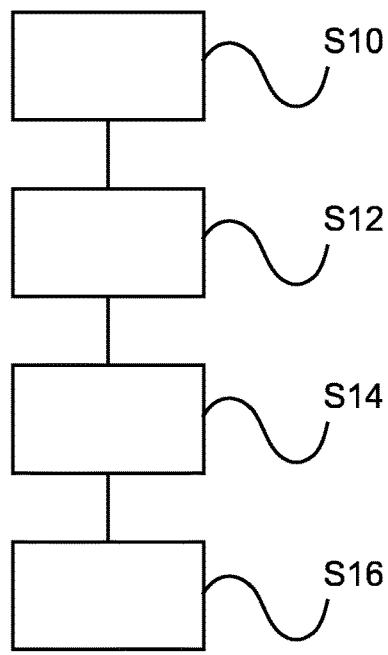
FIG. 2 shows a flow diagram for a method for registration of medical images according to an embodiment of the invention.

FIG. 2 shows a method for registering images that may be performed by the controller 24 or the workstation 30.

It has to be understood that the term "registration" may mean that two images (showing a similar or the same content) are globally moved (rotated, scaled and/or moved) such that their content is overlapping as good as possible.

A medical image may be an image showing interior parts of the human body such as bones, lungs, a heart, vessels, etc. Usually, images acquired with X-ray devices, CT devices or MRT devices in a medical environment such as clinics, doctor's offices, etc. will be medical images.

In step S10, a 2D X-ray image 20 is received in the controller 24 or the workstation 30. For example, the 2D X-ray image 20 may have been acquired with the 2D imaging device 14 and/or may be stored in the database 18 afterwards for loading by the workstation 30.

The X-ray image 20 may have been acquired with the medical 2D imaging device 14 under a specific view direction. A view direction may comprise a view point and a viewing angle, which may be based on an alignment of a detector arrangement (for example attached to the C-arm). The viewing angle may be a two-dimensional angle, for example an altitude and a longitude angle.

In step S12, the 2D X-ray image 20 is filtered, such that specific features and/or landmarks are emphasized and other features and/or landmarks are suppressed.

On the one hand, high frequency components of the 2D X-ray image 20 may be emphasized with respect to low frequency components of the 2D X-ray image. In such a way, low-contrast edges of bone structures matching the amplified frequency components such as spinal discs and thoracic bones may be effectively visualized.

On the other hand, low frequency components may be suppressed with respect to high frequency components. In this way, at the same time, large scale, high-contrast features, such as chest to lung transitions will not be boosted, and may be dimmed. In order to retrain optimal (global) localization such features will not be made completely invisible.

The filtered image may be unsuitable for regular clinical and diagnostic use, however, the filtering may harmonize the image and may enhance the bone ridges, which will be useful in the following registration process.

As an example, the 2D X-ray image 20 may be decomposed into frequency components by a Fourier transform.

A further possibility for boosting specific features is using multi-resolution analysis or Laplace pyramid of the 2D X-ray image 20.

In such a multi-resolution analysis, the 2D X-ray image 20 is decomposed into a set of component images, each component image containing an image content of the 2D X-Ray image relating to a specific resolution. For example, the 2D X-ray image is transformed into a first (lower resolution) component image by averaging over 4 neighboring points. The different image of the original 2D X-ray image 20 and the first low resolution image contains the highest frequency components of the 2D X-ray image 20. Accordingly, a second, third, etc. (lower resolution) component image may be generated and the corresponding difference images contain the second highest, third highest, etc. frequency components of the 2D X-ray image 20.

For emphasizing or suppressing specific frequency components, a brightness and/or a contrast of the corresponding component image may be adjusted.

The brightness and/or the contrast of the corresponding component image may be adjusted by heuristically setting a slope value for the at least one component image.

Here, the term "heuristically" may mean that, based on the estimation that most of the bony landmarks may be most visible in one component image, a first slope value is set to each component image in sequential order. A component image with most response is considered as the component image with most visible bony landmarks. The first slope value is therefore set to such component image. Subsequently, a second slope value is set to the rest of component images in the same manner as mentioned above. In this way, different slope values are set to different component images. Alternatively, different slopes values for different component images can be set simultaneously in order to look for the best combination to boost the bony landmark without overshooting or undershooting the other parts of the image. Note that slope value of the first low resolution image is always set to 1 in order to keep the brightness and/or the contrast of the first low resolution image unchanged. It may render that no substantial portion of the image may get oversaturated or undersaturated.

In the end, the filtered image is generated with the inverse transform, i.e. by adding the component images together.

The resulting filtered image may now be blended/overlaid with other images. The filtering may be tuned such that during the following registration process, the X-ray landmark features are strong enough to remain visible, while not so strong to obfuscate the overlaid image.

In step S14, a 3D image 16 acquired with the medical 3D imaging device 12 is received in the controller 24 or the workstation 30. The 3D image 16 contains the same content as the X-ray image, for example the same part of the patient that is also shown in the X-ray image 20.

From the 3D image 16, a 2D projection image 26 is generated, wherein the 2D projection image 26 is generated with a second view direction, that in a first step may be arbitrary chosen but that will be manipulated in such a way by an operator (such as an physician) that it becomes equal to the first view direction of the 2D X-ray image 20.

It has to be noted that the X-ray image 20 and the 2D projection image 26 may be generated by the same imaging device, such as the controller 24 or by different devices, such as the controller 24 and the workstation 30.

After that, the filtered X-ray image 20 and the 2D projection image 26 are overlaid and displayed on the display device 28.

In step S16, the image processing device helps the operator in registering/aligning the 3D image 16 with the X-ray image 20 by providing functionality for changing the second view direction, such that the 2D projection image 20 is registered with the filtered 2D X-ray image.

In general, the operator may view the difference or missing overlap between the filtered X-ray image 20 and the 2D projection image 26 and may accordingly change the second view direction, such that the overlap is getting better. Due to the change of the second view direction, the 2D projection image 26 is recalculated, overlaid and displayed with the changed view direction as described with respect to step S14.

A changed second view direction may be selected by the operator by translating, rotating and scaling a viewport on the 3D image 16, which may comprise a point of the viewer location and a direction, in which the viewer is viewing. Such parameters may be manipulated with user inputs from the input device 32.

The following figures show, how the filtering of the X-ray images may facilitate the registration process.

FIG. 3A shows an unfiltered X-ray image 20 with a CT overlay image 26 seen from a 30 degree angle. FIG. 3B shows the corresponding filtered X-ray image with the CT overlay image 26. The spinal disks and thoracic bones are outlined and emphasized. The dots indicate with "Landmark" are used for moving the overlay image 26. For example, an operator may select them with a mouse input device and move them accordingly.

FIGS. 4A and 4B show similar images as FIGS. 3A and 3B. However, the X-ray images 20 and the CT overlay image 26 are seen from a −30 degree angle.

It has to be noted that the 3D image 16 may be registered with two X-ray images, for example as shown in FIGS. 3B and 4B. In this case, two 2D X-ray images 20 are received that are acquired under different first view directions with the 2D imaging device 14. For example, an operator may move the C-arm to a first position and may acquire a first X-ray image 20 and then move the C-arm to a second position and may acquire a second X-ray image 20. Furthermore, two 2D projection images 26 are generated from the 3D image 16 under second view directions and the first 2D X-ray image 20 is overlaid with a first of the two 2D projection images 26 and the second 2D X-ray image 20 is overlaid with a second of the two 2D projection images.

Both overlay images (as shown in FIGS. 3B and 4B) may then be displayed simultaneously on the same display device 28.

To help the operator for registration of both X-ray images 20 with the 3D volume image 16 (via the two projection images 26), the controller 24 and the workstation 30 provide functionality such that both second view directions are selectable. In such a way, the operator may virtually move the 3D volume (shown by the two 2D projection images 26), until the 2D projection images 26 completely overlap the X-ray images 20.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS 10 system
12 3D imaging device
14 2D imaging device
16 3D image
18 database
20 2D X-ray image
22 C-arm
24 patient
26 2D projection image
28 display device
30 workstation
32 input device

The invention claimed is:

1. A method for registration of medical images, the method comprising:
  receiving a 2D image acquired with a medical 2D imaging device under a first view direction;
  filtering the 2D image, such that high frequency components of the 2D image are emphasized with respect to low frequency components of the 2D image;

receiving a 3D image acquired with a medical 3D imaging device;

generating a 2D projection image from the 3D image, wherein the 2D projection image is generated with a second view direction;

overlaying the filtered 2D image and the 2D projection image;

providing functionality for changing the second view direction, such that the 2D projection image is registered with the filtered 2D image, wherein filtering the 2D image comprises a multi-resolution analysis, in which the 2D image is decomposed into a set of component images, each component image containing an image content of the 2D image relating to a specific resolution, wherein a brightness and/or a contrast of the at least one component image is adjusted for emphasizing and/or suppressing frequency components.

2. The method of claim 1, wherein the brightness and/or the contrast of the at least one component image is adjusted by heuristically setting a slope value for the at least one component image.

3. The method of claim 1, wherein the 2D image is filtered, such that the low frequency components are suppressed with respect to high frequency components.

4. The method of claim 1, wherein the 2D image and the 2D projection image are generated by the same imaging device.

5. The method of claim 1, wherein two 2D images are received that are acquired under different first view directions;

wherein two 2D projection images are generated from the 3D image under second view directions;

wherein functionality is provided such that both second view directions are selectable.

6. The method of claim 5, wherein a first of the two 2D images is overlaid with a first of the two 2D projection images and displayed on a display device and a second of the two 2D images is overlaid with a second of the two 2D projection images and displayed simultaneously on the same display device.

7. The method of claim 1, wherein selecting the second view direction comprises at least one of: translating, rotating and scaling a viewport on the 3D image.

8. The method of claim 1, further comprising:
receiving inputs from an operator indicating, which second view direction is to be selected.

9. The method of claim 1, further comprising:
displaying the filtered 2D image overlaid with the 2D projection image.

10. The method of claim 1, wherein the 2D imaging device is an X-ray device and/or a C-arm device.

11. The method of claim 1, wherein the 3D imaging device is a computer tomography device or a magnetic resonance tomography device.

12. A computer program product comprising a non-transitory computer readable medium encoded with a computer program, which, when being executed by a processor, is adapted for performing the steps of the method of claim 11.

13. A non-transitory computer-readable medium, on which a computer program according to claim 12 is stored.

14. An image processing device, comprising:
a controller for receiving and filtering a 2D image acquired from a medical 2D imaging device, such that high frequency components of the 2D image are emphasized with respect to low frequency components of the 2D image;

the controller further receiving a 3D image from a medical 3D imaging device and generating a 2D projection image from the 3D image, wherein the 2D projection image is generated with a second view direction; and a display overlaying the filtered 2D image and the 2D projection image;

the controller providing functionality for changing the second view direction, such that the 2D projection image is registered with the filtered 2D image, wherein filtering the 2D image comprises a multi-resolution analysis, in which the 2D image is decomposed into a set of component images, each component image containing an image content of the 2D image relating to a specific resolution, wherein a brightness and/or a contrast of the at least one component image is adjusted for emphasizing and/or suppressing frequency components.

* * * * *